United States Patent
Kanemasa et al.

(10) Patent No.: US 11,129,963 B2
(45) Date of Patent: Sep. 28, 2021

(54) MEDICAL INSTRUMENT

(71) Applicant: SUMITOMO BAKELITE CO., LTD., Shinagawa-ku (JP)

(72) Inventors: Kenichi Kanemasa, Akita (JP); Shinetsu Harata, Akita (JP)

(73) Assignee: SUMITOMO BAKELITE CO., LTD., Shinagawa-ku (JP)

(*) Notice: Subject to any disclaimer, the term of this patent is extended or adjusted under 35 U.S.C. 154(b) by 224 days.

(21) Appl. No.: 16/463,164

(22) PCT Filed: Nov. 24, 2017

(86) PCT No.: PCT/JP2017/042204
§ 371 (c)(1),
(2) Date: May 22, 2019

(87) PCT Pub. No.: WO2018/097244
PCT Pub. Date: May 31, 2018

(65) Prior Publication Data
US 2019/0298971 A1  Oct. 3, 2019

(30) Foreign Application Priority Data

Nov. 25, 2016  (JP) .............................. JP2016-229420

(51) Int. Cl.
*A61M 25/01*  (2006.01)
*A61M 25/00*  (2006.01)

(52) U.S. Cl.
CPC .... *A61M 25/0147* (2013.01); *A61M 25/0136* (2013.01); *A61M 25/005* (2013.01); *A61M 25/0108* (2013.01); *A61M 2025/015* (2013.01)

(58) Field of Classification Search
CPC .......... A61M 25/0147; A61M 25/0136; A61M 25/005; A61M 25/0108; A61M 25/0144; A61M 2025/015
See application file for complete search history.

(56) References Cited

U.S. PATENT DOCUMENTS

2015/0094654 A1* 4/2015 Bansal ............ A61M 25/0147
604/95.04
2016/0051796 A1* 2/2016 Kanemasa ........ A61M 25/0009
604/95.04

FOREIGN PATENT DOCUMENTS

JP  7-500755 A   1/1995
JP  2014-188335 A  10/2014
(Continued)

OTHER PUBLICATIONS

International Search Report dated Jan. 9, 2018 in PCT/JP2017/042204 filed on Nov. 24, 2017.

*Primary Examiner* — Theodore J Stigell
*Assistant Examiner* — Daniel Moore
(74) *Attorney, Agent, or Firm* — Oblon, McClelland, Maier & Neustadt, L.L.P.

(57) ABSTRACT

The present disclosure provides a medical instrument, including a tubular main body; a plurality of operating lines; an operating part main body provided on the base end portion of the tubular main body; a bending operating part which is configured to bend a distal portion of the tubular main body; a path defining part which is configured to define a path of the operating line in the bending operating part; and a deviation preventive member which is configured to prevent the operating line from deviating from a path defined by the path defining part; wherein the operating line becomes in a relaxed state when the bending operating part is in a fixation position, while the operating line becomes in a strained state when the bending operating part is in an operation position.

20 Claims, 12 Drawing Sheets

(56) References Cited

FOREIGN PATENT DOCUMENTS

| | | |
|---|---|---|
| JP | 2015-523892 A | 8/2015 |
| JP | 2016-521181 A | 7/2016 |
| WO | WO 93/08869 A1 | 5/1993 |
| WO | WO 2013/190475 | 12/2013 |
| WO | WO 2014/182855 A1 | 11/2014 |

* cited by examiner

MEDICAL INSTRUMENT

TECHNICAL FIELD

The present disclosure relates to a medical instrument.

Priority is claimed on Japanese Patent Application No. 2016-229420, filed on Nov. 25, 2016, the content of which is incorporated herein by reference.

BACKGROUND ART

There is proposed a medical instrument that is capable of bending a distal portion of a tubular main body by pulling an operating line disposed inside the tubular main body made of resin. When this type of medical instrument is inserted into a body cavity such as a blood vessel, it is possible to select an insertion direction by bending the distal portion of the tubular main body at a diverge point of the body cavity.

In this type of medical instrument, typically, a plurality of the operating lines are provided to face each other, and if an operating line positioned in a desired bending direction is selected and pulled and the other operating line is relaxed, the distal portion of the tubular main body is bent while the pulled operating line is toward inside.

The medical instrument including the plurality of operating lines is provided with a bending operating part having a rotating member called as a dial through which the other operating line becomes relaxed when one operating line is pulled. One end portion of each operating line is wound on the dial such that each operating line is fixed to the dial, and if one operating line is pulled by the rotation of the dial, the operating line is capable of becoming relaxed.

The tubular main body is made of a composite of resin and metal, and the operating lines are made of metal. For this reason, the thermal expansion coefficient of the tubular main body is greatly different from the thermal expansion coefficient of the operating lines. Specifically, the thermal expansion coefficient of the tubular main body is approximately 10 times the thermal expansion coefficient of the operating lines.

For this reason, in a process of forming a hydrophilic coating layer on a surface of the tubular main body under high temperature reaction conditions after the assembly molding of the medical instrument, if a catheter is exposed to a high temperature, a tensile force is applied to the operating lines in a tensile direction, and a compressing force, which is a force against the tensile force, is applied to the tubular main body in an axial direction. As a result, a large load is applied to the operating lines or the tubular main body, or before the medical instrument is used for an operation, the operating line may break or the tubular main body is plastically bent, which is a problem.

In order to cope with the problem, a catheter disclosed in PTL 1 is configured such that a bending operating part is provided to be able to slide relative to an operating part main body, when the bending operating part has slid to a distal side, operating lines are in a relaxed state, and when the bending operating part has slid to a proximal side, the operating lines are in a strained state.

If the catheter is exposed to high temperature environments such as when a hydrophilic coating layer is formed on the catheter, the bending operating part is operated to slide to the distal side, and the operating lines become relaxed, thereby preventing a tensile force from being applied to the operating lines.

CITATION LIST

Patent Literature

[PTL 1] Japanese Unexamined Patent Application, First Publication No. 2014-188335

SUMMARY OF INVENTION

Technical Problem

In recent years, the expansion of a usage range of medical instruments requires a medical instrument having a longer tubular main body. In the medical instrument having such long length, the problem becomes more apparent due to a difference in thermal expansion coefficient between the tubular main body and the operating lines under high temperature environments.

For this reason, as disclosed in PTL 1, in the type of medical instrument in which the operating lines are brought into a relaxed state to cope with high temperature environments, the greater the length of the medical instrument is, the more relaxed the operating lines are required to be.

It has become newly clear that the more relaxed the operating lines are, the greater rooms for improvement in the routing of the operating lines become.

The present disclosure has been made in light of the problem, and provides a medical instrument in which a further improvement in the routing of a relaxed operating line is realized.

Solution to Problem

The present disclosure includes the following technical concepts.

(1) There is provided a medical instrument including a tubular main body that is long and flexible; a plurality of operating lines which are inserted into the tubular main body, each of the operating lines having a tip end portion connected to a distal portion of the tubular main body; an operating part main body provided in a base end portion of the tubular main body; a bending operating part which is provided such that the bending operating part is configured to rotate relative to the operating part main body and to slide between a fixation position and an operation position, to which a base end portion of each operating line is fixed, and which bends the distal portion of the tubular main body by individually applying a pulling force to the plurality of operating lines via the rotation of the bending operating part; and a path defining part that defines a path of each operating line inside the bending operating part, in which when the bending operating part is at the fixation position, the operating lines are in a relaxed state, and when the bending operating part is at the operation position, the operating lines are in a state that is more strained than the relaxed state, and the instrument further includes a deviation preventive member that prevents each operating line from deviating from the path defined by the path defining part.

(2) The medical instrument according to (1) further includes a slider which is provided such that the slider is configured to slide relative to the operating part main body between a projection position and a retraction position, and which restricts the rotation of the bending operating part when the slider is at the projection position and allows the rotation of the bending operating part when the slider is at the retraction position, in which the deviation preventive member is provided with a first notched portion through which the slider is configured to pass, and when the slider slides between the projection position and the retraction position, the slider passes through the first notched portion.

(3) In the medical instrument according to (1) or (2), the deviation preventive member is formed as a member separate from the path defining part and is fitted into the path defining part.

(4) In the medical instrument according to any one of (1) to (3), the deviation preventive member is provided with a second notched portion through which the operating lines pass, and a peripheral boundary edge of the second notched portion has a chamfered shape in which the peripheral boundary edge is rounded in a thickness direction of the deviation preventive member.

Advantageous Effects of Invention

In the medical instrument of the present disclosure, each operating line is prevented from deviating from a defined path inside the bending operating part, thereby improving the routing of a relaxed operating line.

DESCRIPTION OF EMBODIMENTS

Hereinbelow, as an example of a medical instrument of an embodiment of the present disclosure, a catheter will be described with reference to the drawings. In all the drawings, the same reference signs will be assigned to the same configuration elements, and duplicated descriptions will be appropriately omitted. In the following description, a catheter will be exemplified as a medical instrument; however, the present disclosure will not be limited to a catheter, and examples of the present disclosure also include other medical instruments such as an endoscope.

Firstly, an outline of a catheter 1 of the embodiment will be described.

Figure 1:
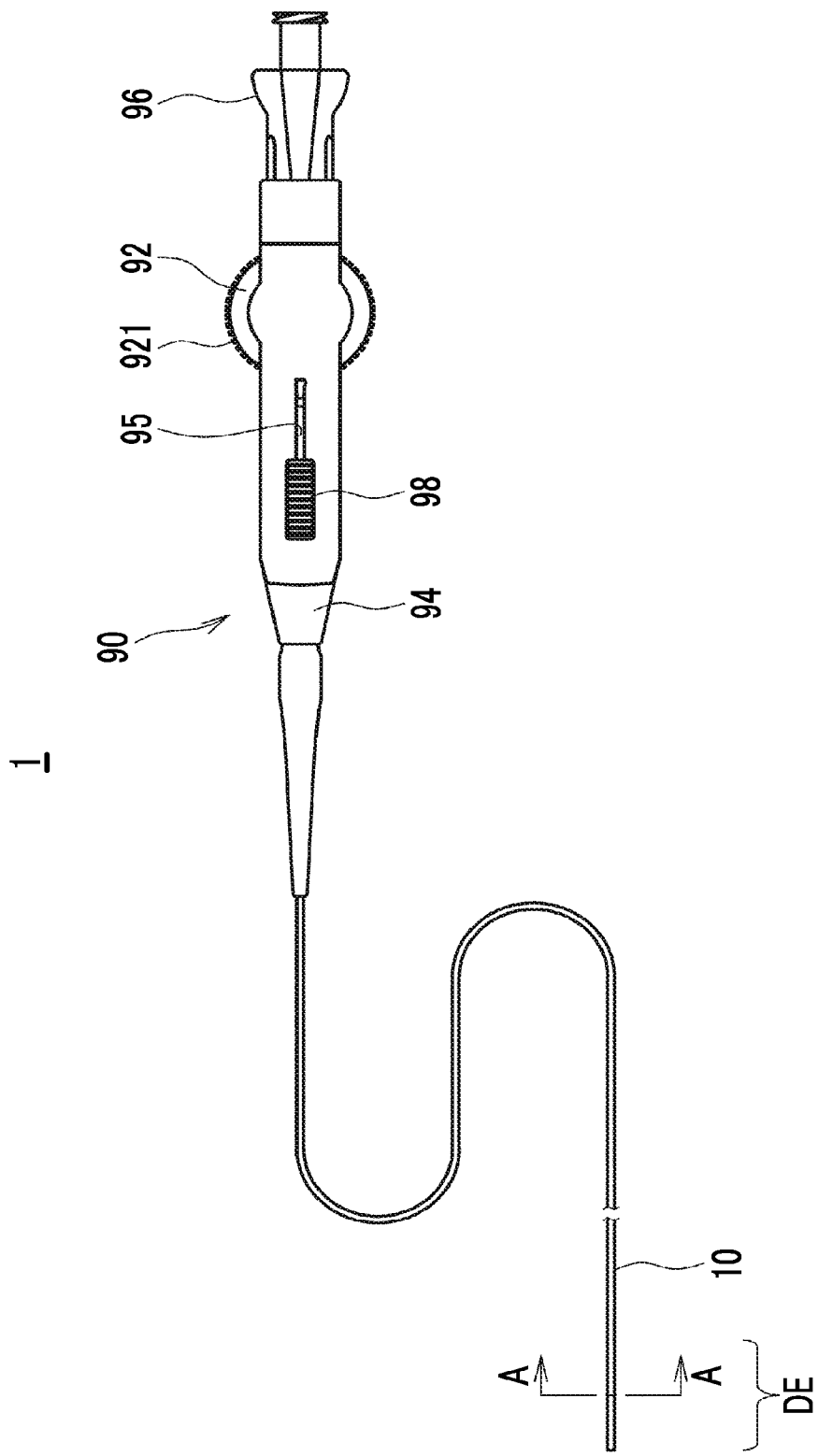
FIG. 1 is an entire side view of a catheter of an embodiment of the present disclosure.
Figure 2:
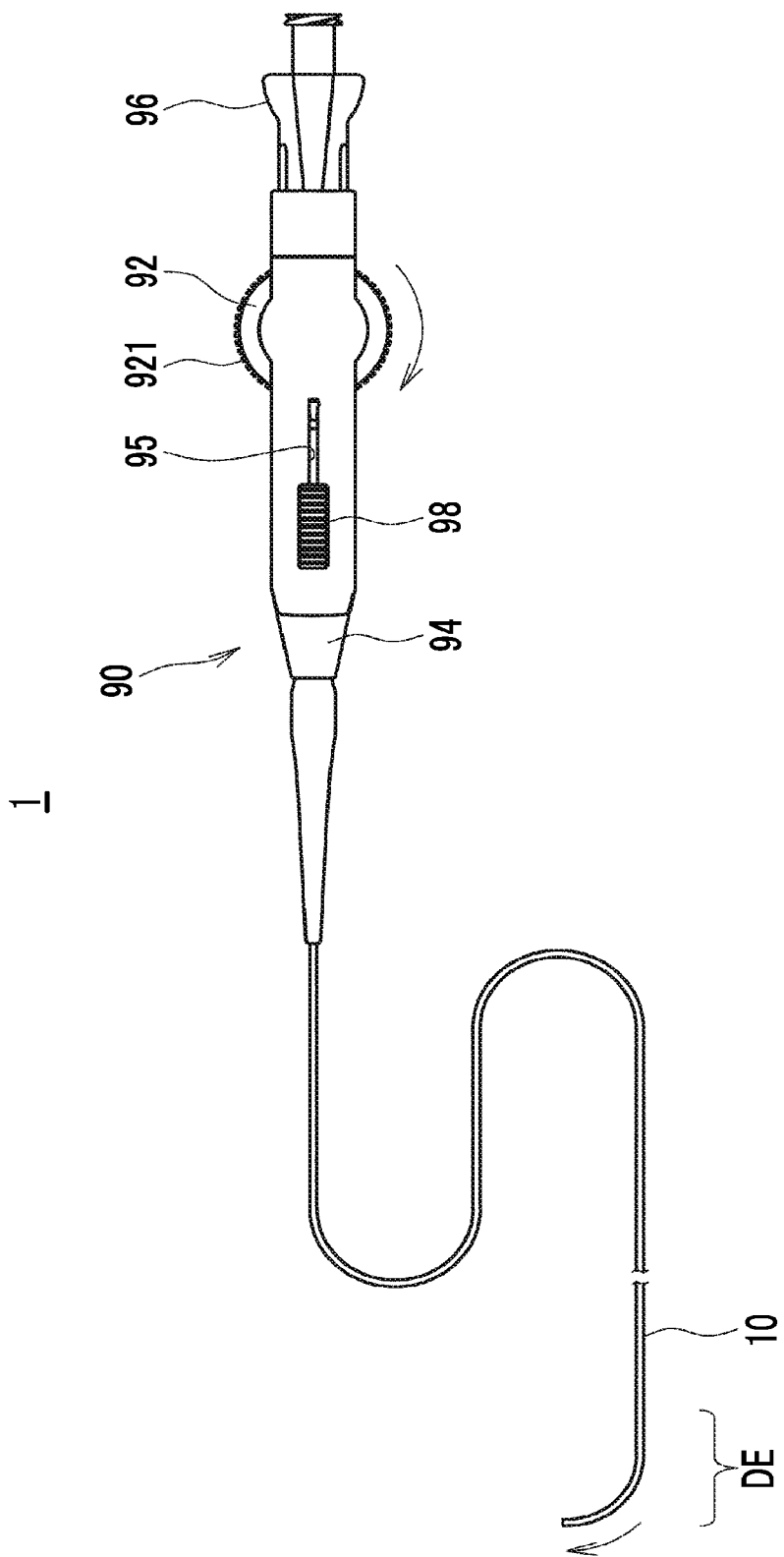
FIG. 2 is an entire side view of the catheter illustrating a state where a bending operating part is operated in one direction.
Figure 3:
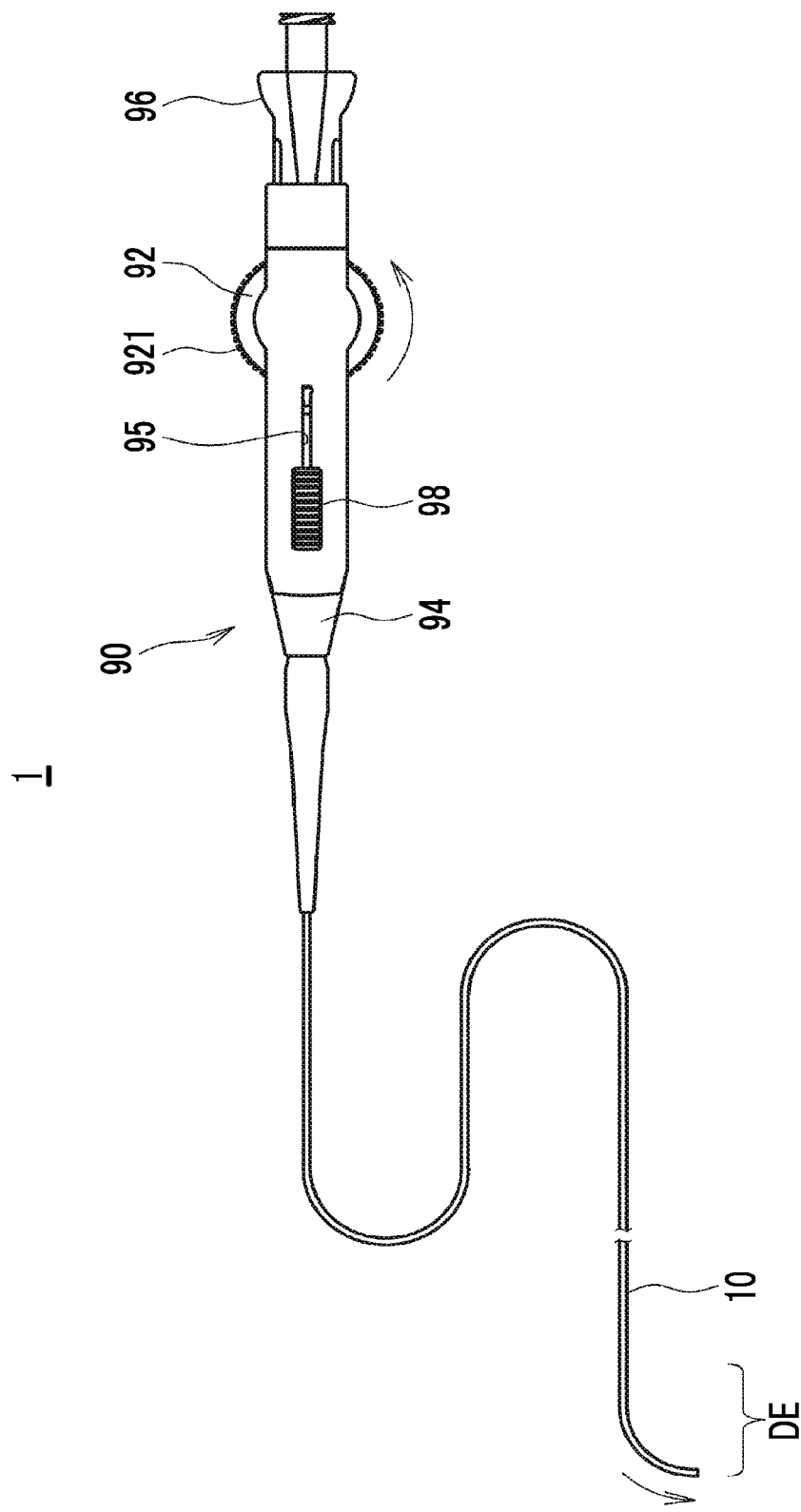
FIG. 3 is an entire side view of the catheter illustrating a state where the bending operating part is operated in the other direction.
Figure 4:
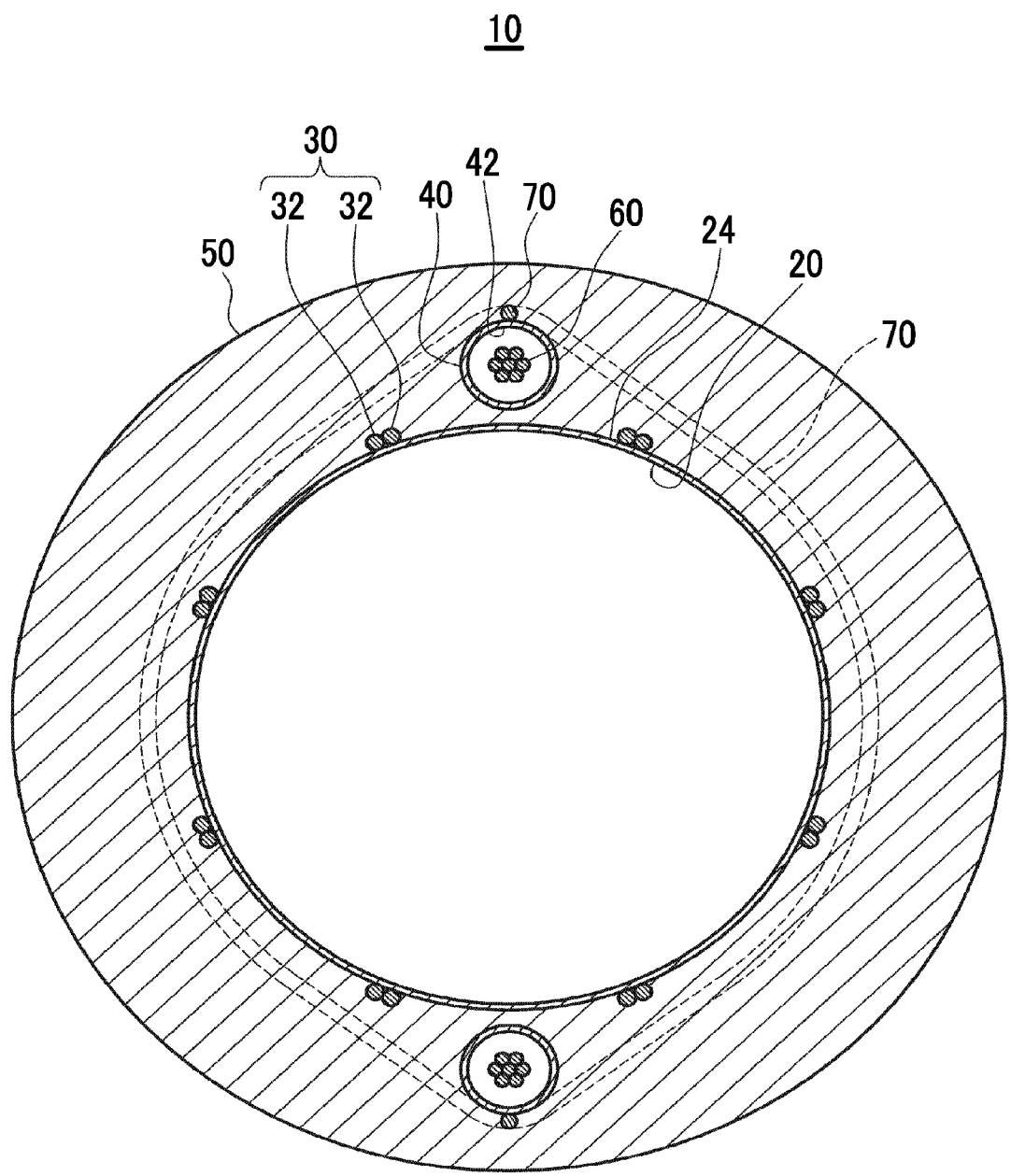
FIG. 4 is a cross-sectional view taken along A-A line in FIG. 1.
Figure 5:
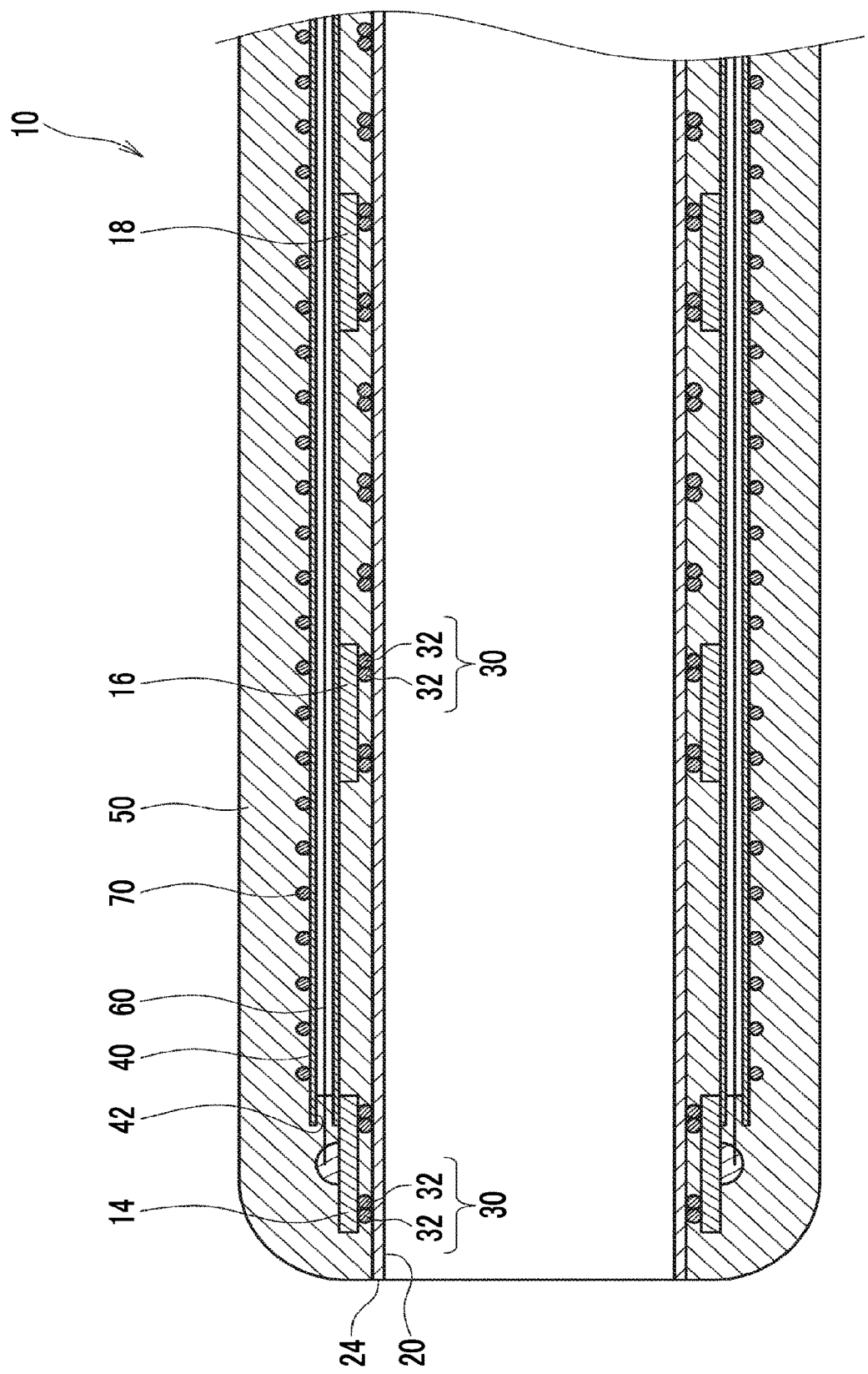
FIG. 5 is a longitudinal cross-sectional view of a distal portion of the catheter.
Figure 6:
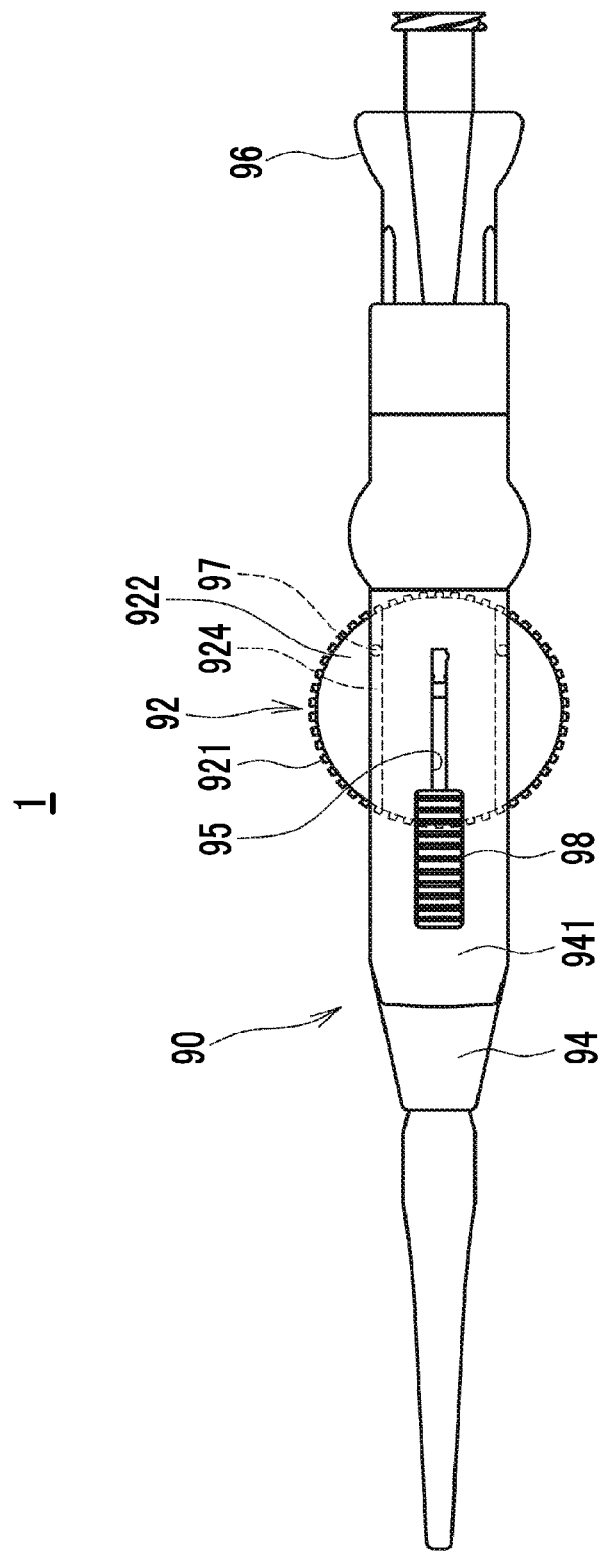
FIG. 6 is a plan view of an operating part when the bending operating part is at a fixation position.
Figure 7:
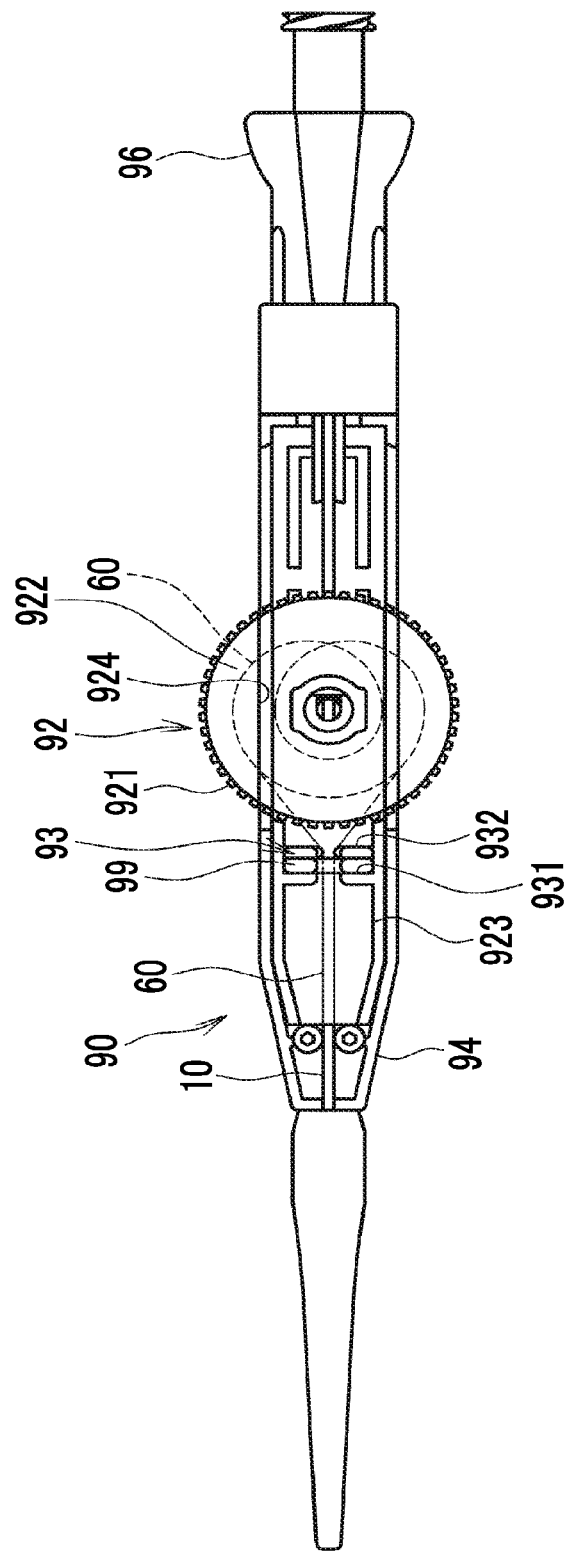
FIG. 7 is a plan view illustrating a state of an operating line when the bending operating part is at the fixation position.
Figure 8:
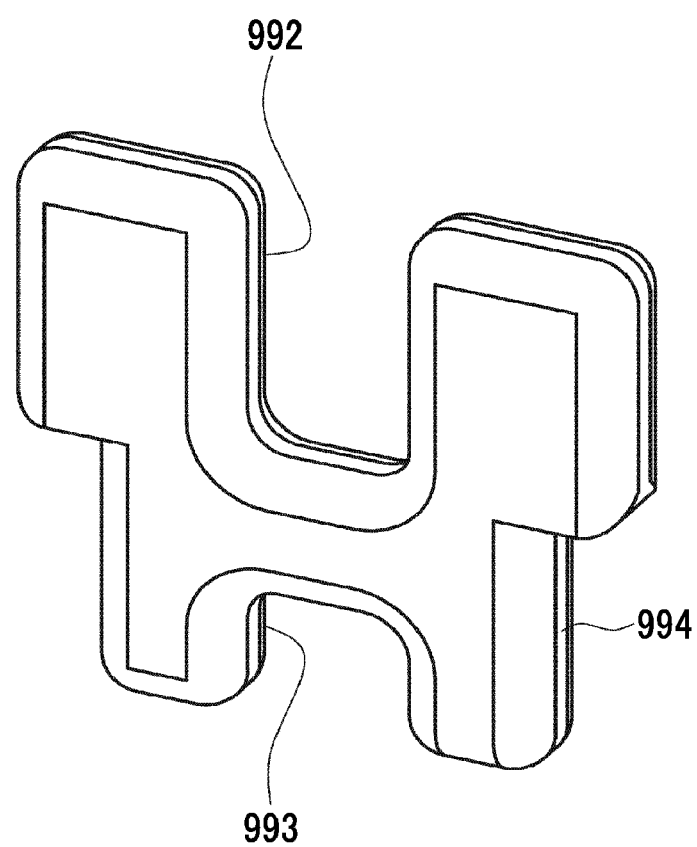
FIG. 8 is a perspective view illustrating a deviation preventive member.
Figure 9:
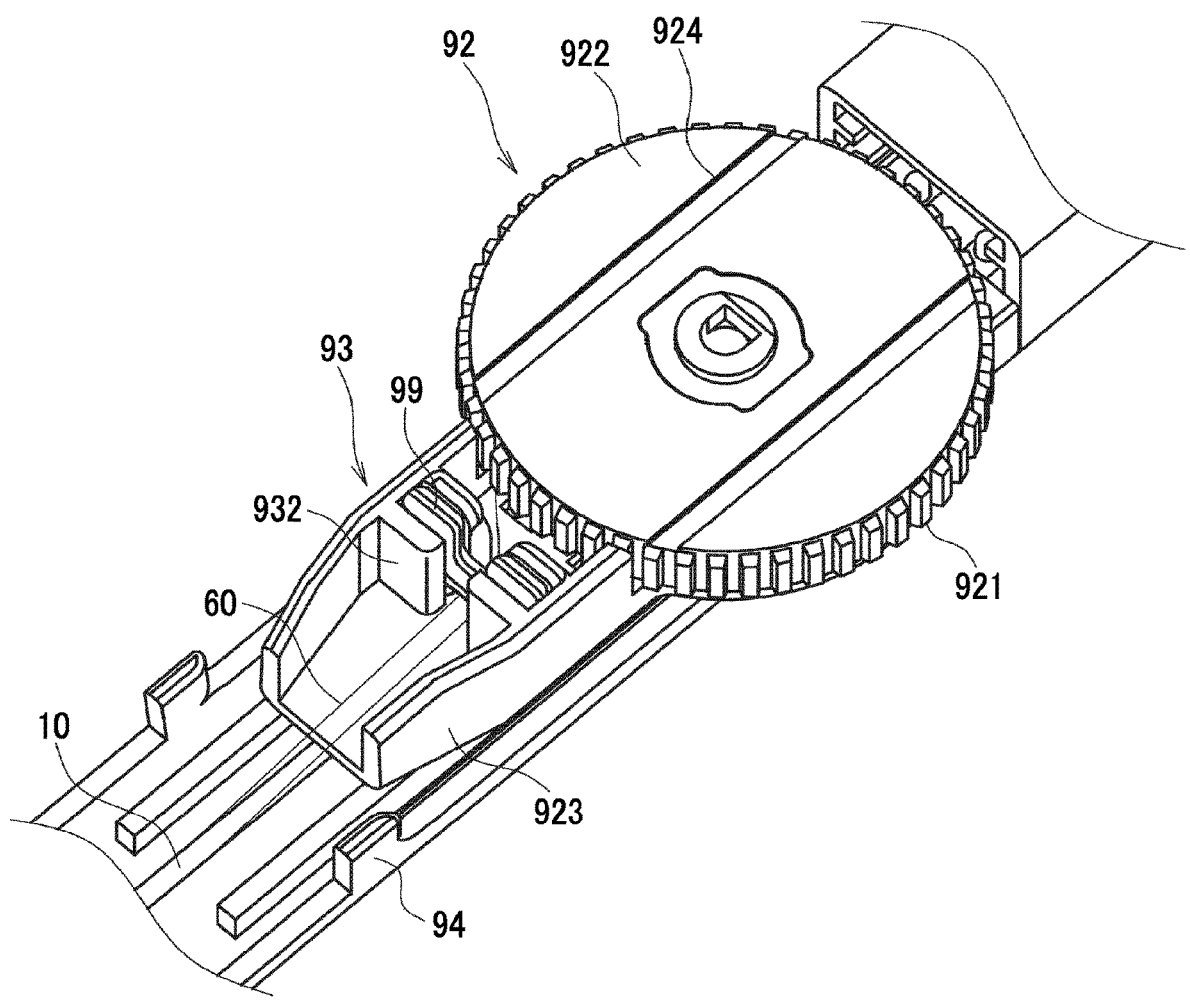
FIG. 9 is a perspective view illustrating a state where a deviation of the operating line is prevented by the deviation preventive member.
Figure 10:
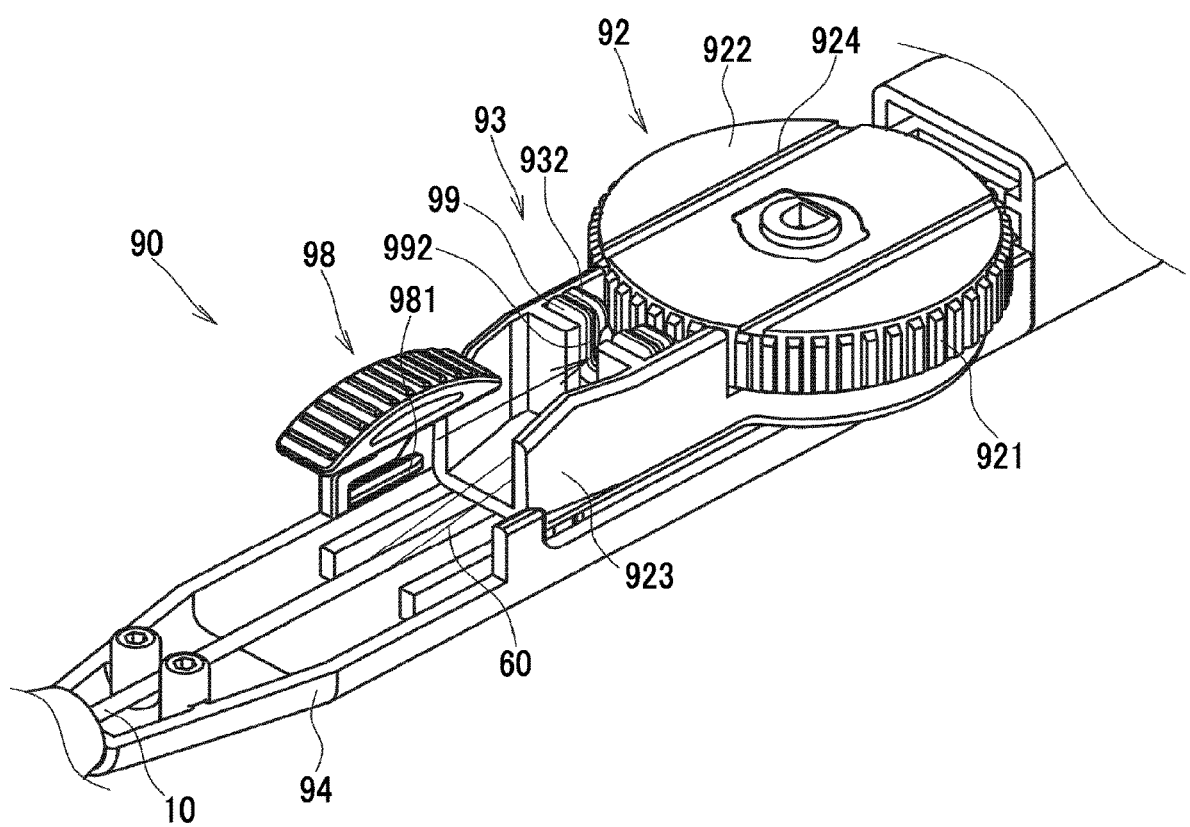
FIG. 10 is a perspective view illustrating an aspect in which a slider passes through a first notched portion of the deviation preventive member.
Figure 11:
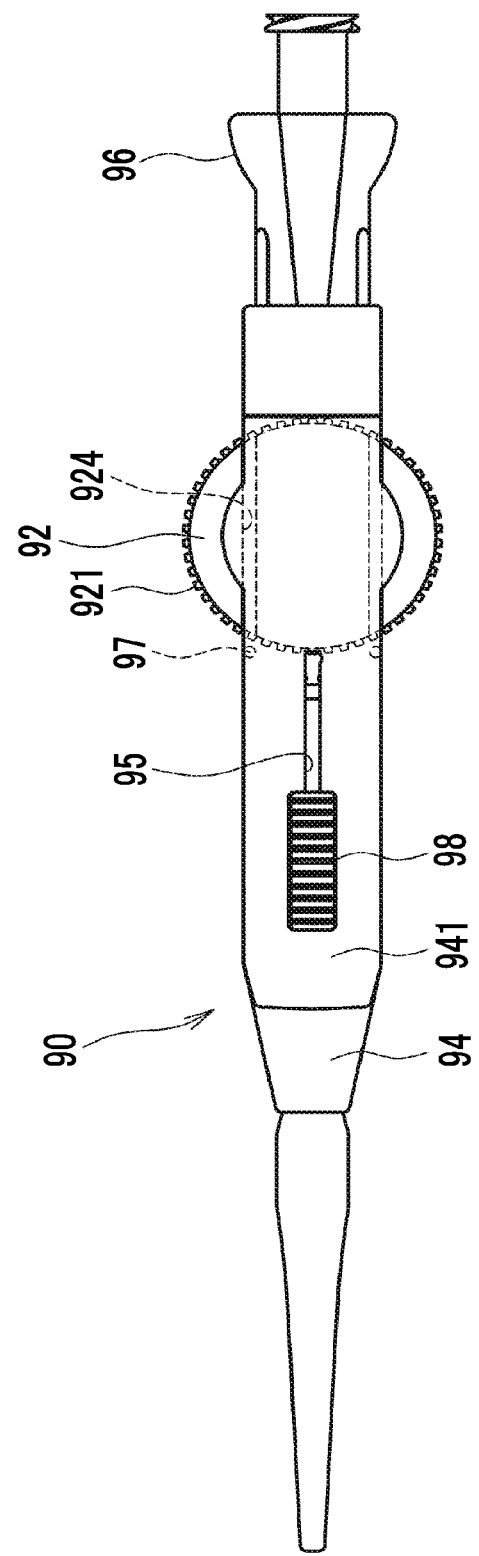
FIG. 11 is a plan view of the operating part when the bending operating part is at an operation position.
Figure 12:
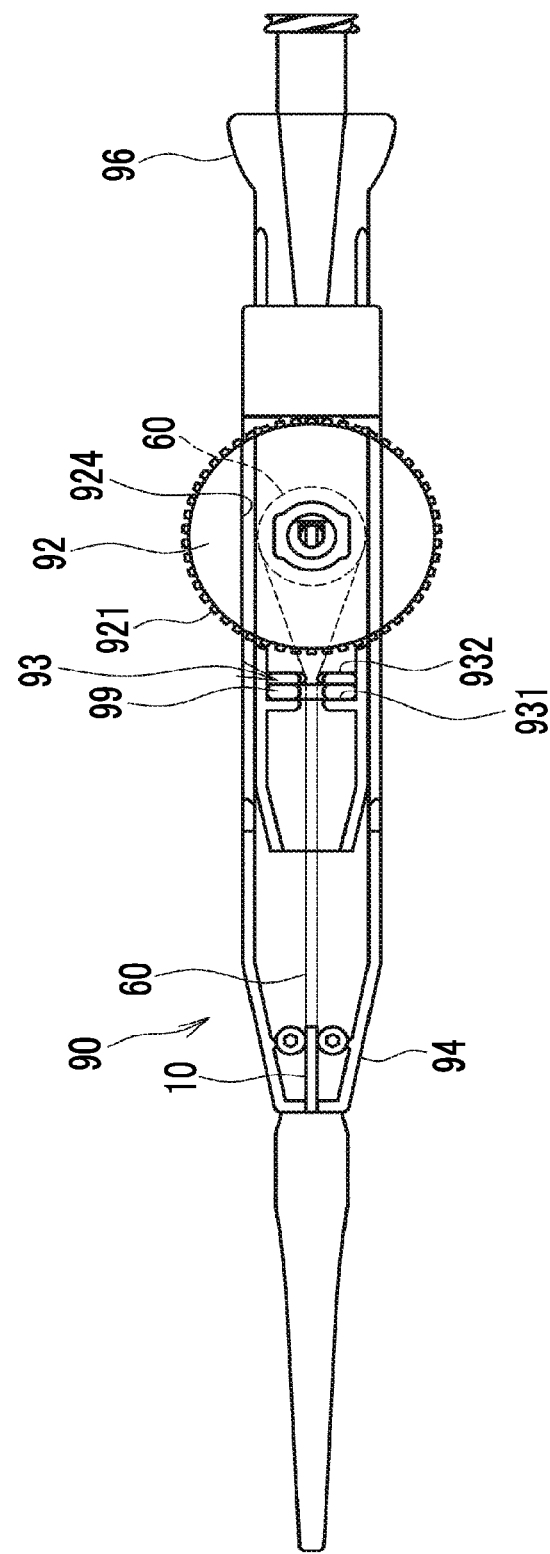
FIG. 12 is a plan view illustrating a state of the operating line when the bending operating part is at the operation position.

FIG. 1 is an entire side view of the catheter 1 of the embodiment of the present disclosure. FIG. 2 is an entire side view of the catheter 1 illustrating a state where a bending operating part 92 is operated in one direction. FIG. 3 is an entire side view of the catheter 1 illustrating a state where the bending operating part 92 is operated in the other direction. FIG. 4 is a cross-sectional view taken along A-A line in FIG. 1. FIG. 5 is a longitudinal cross-sectional view of a distal portion of the catheter 1. FIG. 6 is a plan view of an operating part 90 when the bending operating part 92 is at a fixation position. FIG. 7 is a plan view illustrating a state of an operating line 60 when the bending operating part 92 is at the fixation position. FIG. 8 is a perspective view illustrating a deviation preventive member 99. FIG. 9 is a perspective view illustrating a state where a deviation of the operating line 60 is prevented by the deviation preventive member 99. FIG. 10 is a perspective view illustrating an aspect in which a slider 98 passes through a first notched portion 992 of the deviation preventive member 99. FIG. 11 is a plan view of the operating part 90 when the bending operating part 92 is at an operation position. FIG. 12 is a plan view illustrating a state of the operating line 60 when the bending operating part 92 is at the operation position.

In the catheter 1 illustrated in FIGS. 1 to 3, the left side (side on which an end portion of a tubular main body 10 is positioned) on the drawing sheet is referred to as a distal side, and the right side (side on which the operating part 90 is positioned) on the drawing sheet is referred to as a proximal side.

The catheter 1 includes the tubular main body 10 that is long and flexible; a plurality of the operating lines 60 which are inserted into the tubular main body 10, each of the operating lines 60 having a tip end portion connected to a distal portion DE of the tubular main body 10; and an operating part main body 94 provided in a base end portion of the tubular main body 10.

The catheter 1 includes the bending operating part 92 which is provided such that the bending operating part 92 is configured to rotate relative to the operating part main body 94 and to slide between the fixation position and the operation position, to which a base end portion of each operating line 60 is fixed, and which bends the distal portion DE of the tubular main body 10 by individually applying a pulling force to the plurality of operating lines 60 via the rotation of the bending operating part 92.

When the bending operating part 92 is at the fixation position, the operating lines 60 are in a relaxed state, and when the bending operating part 92 is at the operation position, the operating lines 60 are in a state that is more strained than the relaxed state.

The catheter 1 further includes a path defining part 93 that defines a path of each operating line 60 inside the bending operating part 92, and the deviation preventive member 99 that prevents each operating line 60 from deviating from the path defined by the path defining part 93 (refer to FIGS. 7, 9, and 10).

Subsequently, a configuration of the embodiment will be described in detail.

(Tubular Main Body)

The catheter 1 of the embodiment is an intravascular catheter which is used in such a way that the tubular main body 10 is inserted into a blood vessel.

The tubular main body 10 is referred to as a sheath, and is a long hollow tubular member in which a main lumen 20 is formed as a through hole.

As illustrated in FIG. 5, the tubular main body 10 has a stack structure. The tubular main body 10 is configured such that the main lumen 20 is disposed at the center of the tubular main body 10 and an inner layer (main tube) 24 and an outer layer 50 are stacked on top of each other sequentially from an inner diameter side of the tubular main body 10. A hydrophilic layer (not illustrated) is formed on a surface of the outer layer 50. Each of the inner layer 24 and the outer layer 50 is formed of a flexible resin material, and has a circular tubular shape and substantially a uniform thickness.

The inner layer 24 is an innermost layer of the tubular main body 10, and the main lumen 20 is bounded by an inner wall surface of the inner layer 24. The cross-sectional shape of the main lumen 20 is not limited to a specific shape, and is a circular shape in the embodiment. If the vertical cross section of the main lumen 20 is a circular shape, the diameter of the main lumen 20 may be uniform along a longitudinal direction of the tubular main body 10, or may differ depending on positions in the longitudinal direction.

The inner layer preferably has substantially a uniform thickness from the viewpoint of enabling an easy and accurate assembly.

The inner layer may be formed of the same type of material or different types of materials. The inner layer is preferably formed of the same type of material from the viewpoint of enabling an easy and accurate assembly.

For example, it is possible to use a fluorine thermoplastic polymer resin as the material of the inner layer 24. Specifically, examples of the fluorine thermoplastic polymer resin are capable of including a polytetrafluoroethylene (PTFE) resin, a polyvinylidene fluoride (PVDF) resin, and a perfluoroalkoxy (PFA) resin. If the inner layer 24 is formed of a fluorine polymer material, a drug solution or the like is well delivered when being supplied via the main lumen 20. A sliding resistance when a guide wire or the like is being inserted into the main lumen 20 is reduced.

A wire reinforced layer 30 is a protective layer which is provided closer to the inner diameter side in the tubular main body 10 than the operating lines 60, and which protects the inner layer 24. Because the wire reinforced layer 30 is present closer to the inner diameter side than the operating lines 60, the operating lines 60 are capable of being prevented from penetrating through the layers from the outer layer 50 to the inner layer 24, and being exposed to the main lumen 20.

The wire reinforced layer 30 is formed by winding a reinforcing wire 32. As the material of the reinforcing wire 32, in addition to a metallic material such as tungsten (W), a stainless steel (SUS), a nickel-titanium alloy, a steel, titanium, copper, a titanium alloy or a copper alloy, it is possible to use a resin material such as polyimide (PI), polyamideimide (PAI) or polyethylene terephthalate (PET) which has a shear strength greater than that of each of the inner layer 24 and the outer layer 50. A metallic material is preferably used as the material of the wire reinforced layer 32. In the embodiment, a thin stainless steel wire is used as the material of the reinforcing wire 32.

The wire reinforced layer 30 is a mesh layer. Because a layer beneath each of a first marker 14, a second marker 16, and a third marker 18 is the wire reinforced layer 30 that is formed as a mesh layer resistant to a mechanical deformation, each of the first marker 14, the second marker 16, and the third marker 18 is capable of being fixed to the wire reinforced layer 30 via caulking.

The number of turns of the reinforcing wire 32 of the wire reinforced layer 30 is not limited to a specific number of turns. The embodiment illustrates that the wire reinforced layer 30 is formed of 16 turns of the reinforcing wire 32.

The distal portion DE of the tubular main body 10 is provided with the first marker 14, and the second marker 16 that is positioned closer to the proximal side than the first marker 14. The first marker 14 and the second marker 16 are ring-shaped member containing a radiopaque metallic material such as platinum which does not allow X-rays to penetrate therethrough. Because the positions of two markers, that is, the first marker 14 and the second marker 16 are used as indexes, the position of a tip end of the tubular main body 10 inside a body cavity (blood vessel) is capable of being visualized by radiation beam (X-ray) observation. Therefore, an operator is capable of easily determining an optimal timing for bending the catheter 1.

The third marker 18 is provided closer to the proximal side than the second marker 16. The third marker 18 also is an indicator for the operation of the catheter 1. The embodiment illustrates that a side surface (positioned on the distal side) of the third marker 18 is positioned apart by 30 mm from the tip end of the tubular main body 10.

If the catheter 1 is used to introduce a detachable coil into the body of a subject, an operator is capable of understanding the cut position of the detachable coil inside the main lumen 20 of the catheter 1 by using the third marker 18 as a reference point. The detachable coil refers to a coil that indwells inside the body of the subject to embolize an aneurysm or thrombus of the subject. It is possible to cut the detachable coil at a predetermined cut position by energizing the detachable coil inside the main lumen 20.

In the embodiment, all of the first marker 14, the second marker 16, and the third marker 18 are members which contain the same material and have the same shape.

Because the first marker 14, the second marker 16, and the third marker 18 are made of the same member, it is possible to manufacture the first marker 14, the second marker 16, and the third marker 18 using a common mold, and compared to when the first marker 14, the second marker 16, and the third marker 18 are made of members having different shapes, respectively, it is possible to reduce manufacturing costs.

The wire reinforced layer 30 is formed in the layer beneath each of the first marker 14, the second marker 16, and the third marker 18, and is not formed in a region between the first marker 14 and the second marker 16. The region is referred to as a non-forming region in which the wire reinforced layer 30 is not formed.

There is a discontinuity in the flexural rigidity of the tubular main body 10 between the region in which the wire reinforced layer 30 is not formed and a region in which the wire reinforced layer 30 is formed. The flexural rigidity in the non-forming region in which the wire reinforced layer 30 is not formed is less than the flexural rigidity in the region in which the wire reinforced layer 30 is formed. For this reason, when the operating line 60 is pulled, the tubular main body 10 is capable of being sharply bent in the non-forming region in which the wire reinforced layer 30 is not formed.

In the embodiment, the wire reinforced layer 30 is a mesh layer that is more resistant to a mechanical deformation than the inner layer 24, and is provided in the layer beneath each of the first marker 14, the second marker 16, and the third marker 18. Therefore, each of the first marker 14, the second marker 16, and the third marker 18 is capable of being fixed to the wire reinforced layer 30 via caulking, and is capable of being prevented from detaching therefrom after being fixed.

A sub-tube 40 is a hollow tubular member that bounds a secondary lumen 42. The sub-tube 40 is embedded inside of the outer layer 50. The sub-tube 40 is capable of being formed of a thermoplastic polymer material. An example of the thermoplastic polymer material is a low frictional resin material such as polytetrafluoroethylene (PTFE), polyetheretherketone (PEEK), or a tetrafluoroethylene/hexafluoropropylene copolymer (FEP). The sub-tube 40 is formed of a material having a flexural rigidity and a tensile modulus greater than the flexural rigidity and the tensile modulus of the outer layer 50.

An outer surface of the sub-tube 40 is subject to an etching treatment such as a metal sodium treatment or a plasma treatment. Therefore, adhesion between the sub-tube 40 and the outer layer improves.

As illustrated in FIGS. 4 and 5, two sub-tubes 40 are disposed in the surroundings of the wire reinforced layer 30 while being 180 degrees opposite to each other. The operating lines 60 are inserted into two sub-tubes 40, respectively. Two sub-tubes 40 are parallel to an axial direction of the tubular main body 10.

Two sub-tubes 40 are disposed on the same circumference to surround the main lumen 20. Instead of two sub-tubes 40 being provided as in the embodiment, three or four sub-tubes 40 may be disposed in the surroundings of the main lumen 20 while being equally spaced from each other. In this case, the operating lines 60 may be disposed for all of the sub-tubes 40, respectively, or the operating lines 60 may be disposed for part of the sub-tubes 40.

The operating lines 60 are loosely and slidably inserted into the sub-tubes 40, respectively. A tip end portion of each of the operating lines 60 is fixed to the distal portion DE of the tubular main body 10. If the operating line 60 is pulled toward a base end side, because tubular main body 10 is subject to a tensile force toward a position offset relative to an axis of the tubular main body 10, the tubular main body 10 is bent. Because the operating line 60 of the embodiment is extremely thin and highly flexible, even though the operating line 60 is pushed toward the distal side, a pushing force is not actually applied to the distal portion DE of the tubular main body 10.

The operating line 60 may be formed of a single wire, or may be a stranded wire formed by twisting together a plurality of thin wires.

As the material of the operating line 60, it is possible to use a metallic wire such as a low carbon steel wire (piano wire), a stainless steel (SUS) wire, a corrosion-resistant coated steel wire, a titanium wire, a titanium alloy wire, or a tungsten wire. As the material of the operating line 60, in addition to the foregoing materials, it is possible to use a polymer fiber such as polyvinylidene fluoride (PVDF), high-density polyethylene (HDPE), poly (paraphenylene benzobisoxazole) (PBO), polyetheretherketone (PEEK), polyphenylene sulfide (PPS), polybutylene terephthalate (PBT), polyimide (PI), polytetrafluoroethylene (PTFE), or a boron fiber.

The tip end portion of the operating lines 60 is fixed to an outer circumferential part of the first marker 14. A method of fixing the operating line 60 to the first marker 14 is not limited to a specific method. Examples of the fixing method are capable of including soldering, heat fusion, bonding via an adhesive, and mechanical latching between the operating line 60 and the first marker 14. In the embodiment, the operating line 60 is fixed to the outer circumferential part of the first marker 14 via soldering.

A holding wire 70 is wound around all of the sub-tubes 40, the first marker 14, the second marker 16, the third marker 18, and the wire reinforced layers 30. The holding wire 70 is formed around the sub-tubes 40 by coil winding or mesh braiding.

The holding wire 70 of the embodiment is a coil, more specifically, a coil (multiple-turn coil) formed by winding a plurality of strands.

The holding wire 70 is spirally wound to surround the outside of a pair of the sub-tubes 40 that are disposed in the surroundings of the main lumen 20 while facing each other. In the embodiment, the winding shape of the holding wire 70 is a substantially elliptical shape or a substantially rhombus shape, the large diameter of which is the same as an alignment direction of the sub-tube 40. In FIG. 4, the holding wire 70 having a substantially rhombus shape as the winding shape is illustrated by the dotted line. The holding wire 70 is in contact with a circumferential surface (specifically, outside surface equivalent to an opposite side of the axis of the main lumen 20) of each of the sub-tubes 40. The substantially rhombus shape implies a shape in which a first diagonal line is longer than a second diagonal line, and the first diagonal line is substantially perpendicular to the second diagonal line. The substantially rhombus shape referred to herein includes a kite shape, or a flat polygonal shape such as a flat hexagonal shape or flat octagonal shape in addition to a rhombus shape. The substantially elliptical shape includes an eccentric circular shape such as an egg shape in addition to an elliptical shape or oval shape.

In a forming region in which the wire reinforced layers 30 are formed, the holding wire 70 is in contact with an outer surface of the wire reinforced layer 30 on both sides or a single side in a small-diameter direction perpendicular to the large-diameter direction.

An inside surface of each of the sub-tubes 40 is in contact with an outer surface of each of the first marker 14, the second marker 16, and the third marker 18 (refer to FIG. 5). The holding wire 70 is spirally wound on the pair of sub-tubes 40 while being in contact with the outside surface of each of the sub-tubes 40. The holding wire 70 is wound on the sub-tubes 40 over the entire length of the sub-tubes 40 in the longitudinal direction of the tubular main body 10.

Therefore, the holding wire 70 is wound around all of the sub-tubes 40, the first marker 14, the second marker 16, the third marker 18, the wire reinforced layers 30 that are the layers beneath the first marker 14, the second marker 16, and the third marker 18, such that the sub-tubes 40, the first marker 14, the second marker 16, the third marker 18, and the wire reinforced layers 30 are in close contact with each other without being loosely joined together. For this reason, even after a process of forming the outer layer 50, the sub-tubes 40 are capable of highly accurately keeping parallel to the first marker 14, the second marker 16, and the third marker 18, or parallel to the wire reinforced layers 30, and the position of each of the sub-tubes 40 is capable of being prevented from being offset. The position of each of the sub-tubes 40 is more effectively prevented from being offset because a tightening force increases by virtue of the holding wire 70 being a multiple-turn coil.

Any one of the metallic materials or the resin materials capable of being used as the material of the reinforcing wire 32 is capable of being used as the material of the holding wire 70. A metallic material is preferably used as the material of the holding wire 70. In the embodiment, the holding wire 70 contains a different type of material which is not contained in the reinforcing wire 32. The ductility of the holding wire 70 is preferably greater than the ductility of the reinforcing wire 32. Specifically, as the material of the holding wire 70, it is possible to use a soft austenitic stainless steel (W1 or W2) that is a annealed material, copper, or a copper alloy, and as the material of the reinforcing wire 32, it is possible to use a tungsten or stainless spring steel.

Because a highly ductile material is used as the material of the holding wire 70, when the holding wire 70 is formed around the sub-tubes 40 by coil winding or mesh braiding (coil winding in the embodiment), the holding wire 70 plastically stretches and deforms without the winding of the holding wire 70 being loose, thereby fixing the sub-tubes 40.

A proximal end of the wire reinforced layer 30 is positioned inside a proximal end of the tubular main body 10, that is, inside the operating part 90.

A distal end of the inner layer 24 may reach a distal end of the tubular main body 10, or may end at a position that is away from the distal end toward the base end side. The position where the inner layer 24 ends may be inside a region in which the first marker 14 is provided.

The outer layer 50 is a part having a circular tubular shape which mainly forms a thickness of the tubular main body 10. The wire reinforced layer 30, the first marker 14, the second marker 16, the third marker 18, the sub-tube 40, and the holding wire 70 are provided inside of the outer layer 50 sequentially from the inner diameter side. The wire reinforced layers 30, the first marker 14, the second marker 16, the third marker 18, and the holding wire 70 are disposed coaxially with the tubular main body 10.

The outer layer preferably has substantially a uniform thickness from the viewpoint of enabling an easy and accurate assembly.

The outer layer may be formed of the same type of material or different types of materials. The outer layer is preferably formed of the same type of material from the viewpoint of enabling an easy and accurate assembly.

It is possible to use a thermoplastic polymer material as the material of the outer layer 50. Examples of the thermoplastic polymer material are capable of including nylon elastomers such as polyimide (PI), polyamideimide (PAI), polyethylene terephthalate (PET), polyethylene (PE), polyamide (PA), a polyamide elastomer (PAE), polyether block amide (PEBA), and including polyurethane (PU), an ethylene-vinyl acetate (EVA) resin, polyvinyl chloride (PVC), and polypropylene (PP).

Inorganic fillers may be mixed in the outer layer 50. A contrast agent such as barium sulfate and bismuth subcarbonate is capable of being an example of the inorganic filler. The mixing of the contrast agent in the outer layer 50 is capable of improving the X-ray contrast properties of the tubular main body 10 inside a body cavity.

(Operating Part)

As illustrated in FIGS. 6 and 7 and FIGS. 9 to 12, the operating part 90 has the operating part main body 94 which a user grips by the hand, and the bending operating part 92 which is provided such that the bending operating part 92 is configured to rotate and slide relative to the operating part main body 94. The base end portion of the tubular main body 10 is introduced into the operating part main body 94.

The operating part main body 94 has an inner space, and a sliding mechanism for slidably holding the bending operating part 92 is provided in the inner space.

The operating part main body 94 includes a hub 96 provided to communicate with the main lumen 20 of the tubular main body 10. A syringe (not illustrated) is mounted in the hub 96. The hub 96 is provided in a rear end portion of the operating part main body 94, and the syringe is mounted in the hub 96 from a rear side of the hub 96. A user is capable of supplying a drug solution or the like into a body cavity of a subject via the main lumen 20 by injecting the drug solution or the like into the hub 96 via the syringe. Examples of the drug solution are capable of including a medical device such as a detachable coil or beads (spherical embolic substance) in addition to drug solutions such as a contrast agent, anticancer liquid, a physiological saline solution, and n-butyl-2-cyanoacrylate (NBCA) used as an instant adhesive.

The operating lines 60 and the sub-tubes 40 diverge from the tubular main body 10 in a front end portion of the inner space of the operating part main body 94, respectively. The base end portion of each of the operating lines 60, which lead out of two sub-tubes 40, respectively, is connected to a dial 922 of the bending operating part 92.

The bending operating part 92 includes the dial 922 which individually pulls the plurality of operating lines 60, and a dial supporting part 923 which supports the dial 922 and is engaged with the sliding mechanism of the operating part main body 94 to move the bending operating part 92 from the fixation position to the operation position.

A gap is formed on a distal side of the dial 922 between an upper edge of the dial supporting part 923 and an inner surface of a main body cover 941. The gap is greater than a wire diameter of each of the operating lines 60, and the operating lines 60 are routed in the gap.

A latching claw (not illustrated) is provided in the dial supporting part 923 of the bending operating part 92. When the bending operating part 92 slides from the fixation position to the operation position, the latching claw becomes engaged with a recessed latching portion (not illustrated) provided on an inner peripheral surface of the operating part main body 94, thereby preventing the bending operating part 92 from returning from the operation position to the fixation position.

The bending operating part 92 is at the fixation position when the hydrophilic layer is being formed on the surface of the outer layer 50. The catheter 1 may be shipped out of a factory after the bending operating part 92 is moved from the fixation position to the operation position, or the bending operating part 92 may be at the fixation position when the catheter 1 is shipped out the factory, and may be moved from the fixation position to the operation position right before the catheter 1 is used.

The catheter 1 includes the slider 98 which is provided such that the slider 98 is capable of sliding relative to the operating part main body 94 between a projection position and a retraction position. When the slider 98 is at the projection position, the slider 98 restricts the rotation of the bending operating part 92, and when the slider 98 is at the retraction position, the slider 98 allows the rotation of the bending operating part 92. The deviation preventive member 99 is provided with the first notched portion 992 through which the slider 98 is configured to pass. When the slider 98 slides between the projection position and the retraction position, the slider 98 passes through the first notched portion 992.

The slider 98 is engaged with a recessed portion 95 provided in the main body cover 941. The recessed portion 95 is a slit which penetrates through the main body cover 941 and extends in a tip end-to-base end direction. A protrusion 981 of the slider 98 is accommodated in the operating part main body 94 in a state where the protrusion 981 is inserted into the recessed portion 95.

Because the slider 98 is configured to pass through the first notched portion 992 of the deviation preventive member 99 when the slider 98 slides between the projection position and the retraction position, the member, that is, the slider 98 is capable of being disposed to align with a longitudinal direction of the operating part main body 94, and the diameter of the operating part main body 94 is capable of being prevented from increasing. Because the first notched portion 992 is provided in the deviation preventive member 99, even though the member, that is, the slider 98 is disposed to align with the longitudinal direction of the operating part main body 94, the slider 98 is capable of being prevented from interfering with the deviation preventive member 99.

As illustrated in FIG. 10, the protrusion 981 is formed in a tip end portion of the slider 98, which is a lower portion of the slider 98 and is toward the dial 922. The protrusion 981 has a diameter less than an opening width of a toothed engaging portion (knurled portion having wave-like vertically ridges) 921 formed in a circumferential surface of the dial 922. For this reason, if the slider 98 slides to the dial 922, the protrusion 981 latches onto the circumferential surface of the dial 922, and the rotation of the dial 922 is restricted. Therefore, the dial 922 is capable of being restricted from rotating in a state where the distal portion DE of the tubular main body 10 is bent, and the catheter 1 is capable of maintaining a bent state.

The path defining part 93 and the deviation preventive member 99 are provided in the gap such that the path defining part 93 defines a routing path of each of the operating lines 60, and the deviation preventive member 99 is fitted into the path defining part 93 to prevent the operating lines 60 from deviating from the path defining part 93. A proximal side end portion of the operating line 60 is wound on the dial 922 such that the operating line 60 is fixed to the dial 922.

Because the deviation preventive member 99 is provided, even though the operating line 60 becomes relaxed, the operating line 60 is prevented from climbing over a rib-shaped portion 932, and entering the gap.

The deviation preventive member 99 is formed as a member separate from the path defining part 93, and is fitted into the path defining part 93.

Because the deviation preventive member 99 and the path defining part 93 are formed as separate members, respectively, in a process of manufacturing the catheter 1, it is possible to fit the deviation preventive member 99 into the path defining part 93 after routing the operating lines 60 in the path defining part 93. Therefore, it is easy to route the operating lines 60, and it is possible to improve ease of manufacturing of the catheter 1.

The path defining part 93 is formed of four rib-shaped portions 932 provided in the surroundings of the respective routing paths of the operating lines 60.

Two rib-shaped portions 932 are provided to face an inner peripheral wall of the bending operating part 92, and two other rib-shaped portion 932 are provided to face another inner peripheral wall of the bending operating part 92. Two rib-shaped portions 932 formed on one side are spaced apart from each other, and define another slit 931. Two rib-shaped portions 932 formed on the other side are spaced apart from each other, and define a slit 931. The deviation preventive member 99 is fitted into two slits 931, and thus is fixed to the path defining part 93.

The operating lines 60 pass through between the rib-shaped portions 932 of the path defining part 93, which are disposed to face each other, and thus the respective routing paths of the operating lines 60 are defined inside the operating part main body 94.

The deviation preventive member 99 is a member containing resin and having a substantially H shape, and the first notched portion 992 is provided on one end side of the deviation preventive member 99. The first notched portion 992 is sized such that the protrusion 981 of the slider is capable of passing through the first notched portion 992.

The deviation preventive member is provided with a second notched portion 993 through which the operating lines pass, and a peripheral boundary edge of the second notched portion 993 has a chamfered shape in which the peripheral boundary edge is rounded in a thickness direction of the deviation preventive member.

The second notched portion 993 is rounded, and thus the operating lines 60 passing through the second notched portion 993 are capable of being prevented from being caught by the second notched portion 993.

The first notched portion 992 is formed on an upper side (upper side on the drawing sheet of FIG. 8) of the deviation preventive member 99, and the second notched portion 993 is formed on a lower side (lower side on the drawing sheet of FIG. 8) of the deviation preventive member 99.

Because the deviation preventive member 99 is fitted into the path defining part 93, the operating lines 60 positioned inside the path defining part 93 are capable of being prevented from climbing over and deviating from the path defining part 93. For this reason, when the bending operating part 92 is at the fixation position and the operating lines 60 are relaxed, or when the operating lines relaxed by the rotation of the bending operating part 92, a relaxed part of the operating lines 60 is capable of being prevented from deviating from the path defining part 93, and interfering with other members.

A third notched portion 994 is formed in the deviation preventive member 99 by notching a lower side surface of the deviation preventive member 99. A protrusion (not illustrated) having a complementary shape with respect to the third notched portion 994 is formed inside the slit 931 of the path defining part 93.

If the third notched portion 994 is firstly inserted into the slits 931 to insert the deviation preventive member 99 thereinto, because the third notched portion 994 is provided, it is possible to insert the deviation preventive member 99 into the slits 931 while avoiding interferences between the deviation preventive member 99 and the protrusions. If the first notched portion 992 is firstly inserted into the slits 931 to insert the deviation preventive member 99 thereinto, because the protrusions are provided, the deviation preventive member 99 is blocked from entering the slits 931, and it is not possible to insert the deviation preventive member 99 into the slits 931.

Therefore, when the catheter 1 is manufactured, it is possible to prevent the occurrence of an event where the deviation preventive member 99 is erroneously oriented and fitted into the path defining part 93.

The dial 922 is a circular disk-shaped member having the toothed engaging portion (knurled portion having vertical ridges) 921 formed on a circumferential surface of the circular disk-shaped member. Two engaging grooves 924 are formed in an upper surface of the dial 922, and are parallel to each other while interposing a rotary shaft of the dial 922 therebetween.

Each of the engaging grooves 924 is formed to connect together both end portions of an arc of a circular outer circumference of the dial 922. The engaging groove 924 is formed to have a length greater than a radius of rotation of the dial 922. The width of the engaging groove 924 is sized such that an engaging protrusion 97 formed in the operating part main body 94 is capable of entering the engaging groove 924. Because the engaging groove 924 is formed to have a length greater than the radius of rotation of the dial 922, it is possible to secure the entering length of the engaging protrusion 97 with respect to the engaging groove 924, which is greater than the radius of rotation of the dial 922.

In the present disclosure, the shape of the dial 922 is not limited to a circular disk shape; however, the dial 922 may have an elliptical shape or polygonal shape in a plan view of the dial 922.

The bending operating part 92 is capable of sliding relative to the operating part main body 94 between the distal side (fixation position) and the proximal side (operation position).

When the bending operating part 92 is at the fixation position as illustrated in FIGS. 6 and 7, the engaging protrusions 97 of the operating part main body 94 have been engaged with the engaging grooves 924 formed in the dial 922, respectively. For this reason, the rotation of the dial 922 is restricted by the engaging protrusions 97. At that time, two operating lines 60 are in a relaxed state as illustrated in FIG. 7.

When the bending operating part 92 is at the operation position as illustrated in FIGS. 11 and 12, the engaging protrusions 97 have escaped from the engaging grooves 924, respectively. For this reason, the restriction imposed by the engaging protrusions 97 is released, and the dial 922 is capable of rotating. As illustrated in FIG. 12, at that time, because two operating lines 60 are pulled as the bending operating part 92 slides from the fixation position to the operation position, two operating lines 60 enter a state that is more strained than the relaxed state.

If the dial 922 of the bending operating part 92 at the operation position rotates in any direction, because one of two operating lines 60 is pulled toward the base end side, one operating line 60 is capable of being subject to a tensile force, and the other operating line 60 is capable of becoming loose. Therefore, the pulled operating line 60 bends the distal portion DE of the tubular main body 10.

Specifically, as illustrated in FIG. 2, if the dial 922 rotates in one direction (clockwise direction), one operating line 60 is pulled toward the base end side. A tensile force is applied to the distal portion DE of the tubular main body 10 via one operating line 60. Therefore, the distal portion DE of the tubular main body 10 is bent relative to a datum line, that is, the axis of the tubular main body 10 toward the sub-tube 40 into which one operating line 60 is inserted.

As illustrated in FIG. 3, if the dial 922 rotates around the rotary shaft of the dial 922 in the other direction (counter-clockwise direction), the other operating line 60 is pulled toward the base end side. A tensile force is applied to the distal portion DE of the tubular main body 10 via the other operating line 60. Therefore, the distal portion DE of the tubular main body 10 is bent relative to the datum line, that is, the axis of the tubular main body 10 toward the sub-tube 40 into which the other operating line 60 is inserted.

If two operating lines 60 are selectively pulled by the operation of the dial 922 of the operating part 90, the distal portion DE of the tubular main body 10 is capable of being bent selectively in a first or second direction which is contained in the same plane.

If the operating part 90 rotates around the axis of the tubular main body 10, the distal portion DE of the tubular main body 10 is capable of being subject to torque and rotating at a predetermined angle. Therefore, the direction of the distal portion DE of the catheter 1 is capable of being freely controlled by a combination of the operation of the bending operating part 92 and the rotation of the entirety of the operating part 90 around the axis.

If the magnitude of the rotary angle of the bending operating part 92 is adjusted, the pulling length of the operating line 60 is adjusted to a predetermined length, and thus the bending angle of the distal portion DE of the catheter 1 is capable of being controlled.

For this reason, the catheter 1 is capable of being pushed into and entering a body cavity such as blood vessels diverging at variety angles.

In the present disclosure, the configuration elements of the medical instrument are not necessarily provided as individually independent members. A variety of combinations of configuration elements are allowed, for example, a plurality of configuration elements may be formed of one member, one configuration element may be formed of a plurality of members, a configuration element may be part of another configuration element, or part of a configuration element may be duplicated as part of another configuration element.

INDUSTRIAL APPLICABILITY

The present disclosure is capable of providing the medical instrument in which a further improvement in the routing of a relaxed operating line is realized.

REFERENCE SIGNS LIST

1: catheter
10: tubular main body
14: first marker
16: second marker
18: third marker
20: main lumen
24: inner layer
30: wire reinforced layer
32: reinforcing wire
40: sub-tube
42: secondary lumen
50: outer layer
60: operating line
70: holding wire
90: operating part
92: bending operating part
93: path defining part
94: operating part main body
95: recessed portion
96: hub
97: engaging protrusion
98: slider
99: deviation preventive member
921: toothed engaging portion
922: dial
923: dial supporting part
924: engaging groove
931: slit
932: rib-shaped portion
941: main body cover
981: protrusion
992: first notched portion
993: second notched portion
994: third notched portion
DE: distal portion

The invention claimed is:
1. A medical instrument, comprising:
a flexible tubular main body;
a plurality of operating lines inserted into the flexible tubular main body such that each of the operating lines has a tip end portion connected to a distal portion of the flexible tubular main body; and an operating part comprising an operating part main body positioned in a base end portion of the flexible tubular main body and a bending operating part configured to rotate relative to the operating part main body and to slide between a fixation position and an operation position such that the bending operating part bends the distal portion of the flexible tubular main body by individually applying a pulling force to the plurality of operating lines via rotation of the bending operating part, wherein the operating part includes a path defining part that defines a path of each of the operating lines inside the operating part, and a deviation preventive member that prevents each of the operating lines from deviating from the path defined by the path defining part and has a notched portion through which the operating lines pass, the deviation preventive member is formed such that a peripheral boundary edge of the notched portion has a chamfered shape in which the peripheral boundary edge is rounded in a thickness direction of the deviation preventive member, a base end portion of each of the operating lines is fixed to the bending operating part, when the bending operating part is at the fixation position, the operating lines are in a relaxed state, and when the bending operating part is at the operation position, the operating lines are in a state that is more strained than the relaxed state.

2. The medical instrument according to claim 1, further comprising:

a slider configured to slide relative to the operating part main body between a projection position and a retraction position such that slider restricts the rotation of the bending operating part when the slider is at the projection position and allows the rotation of the bending operating part when the slider is at the retraction position, wherein the deviation preventive member has a notched portion for the slider through which the slider is configured to pass, and when the slider slides between the projection position and the retraction position, the slider passes through the notched portion for the slider.

3. The medical instrument according to claim 2, wherein the deviation preventive member is configured to be fitted into the path defining part.

4. The medical instrument according to claim 3, wherein the path defining part comprises a plurality of rib shaped portions positioned to surround the plurality of operating lines in the paths.

5. The medical instrument according to claim 4, wherein the plurality of rib shaped portions of the path defining part comprises a first pair of rib shaped portions and a second pair of rib shaped portions positioned such that the deviation preventive member is configured to be fitted into a space formed between the first and second pairs of rib shaped portions.

6. The medical instrument according to claim 2, wherein the path defining part comprises a plurality of rib shaped portions positioned to surround the plurality of operating lines in the paths.

7. The medical instrument according to claim 6, wherein the plurality of rib shaped portions of the path defining part comprises a first pair of rib shaped portions and a second pair of rib shaped portions positioned such that the deviation preventive member is configured to be fitted into a space formed between the first and second pairs of rib shaped portions.

8. The medical instrument according to claim 1, wherein the deviation preventive member is configured to be fitted into the path defining part.

9. The medical instrument according to claim 8, wherein the path defining part comprises a plurality of rib shaped portions positioned to surround the plurality of operating lines in the paths.

10. The medical instrument according to claim 9, wherein the plurality of rib shaped portions of the path defining part comprises a first pair of rib shaped portions and a second pair of rib shaped portions positioned such that the deviation preventive member is configured to be fitted into a space formed between the first and second pairs of rib shaped portions.

11. The medical instrument according to claim 1, wherein the path defining part comprises a plurality of rib shaped portions positioned to surround the plurality of operating lines in the paths.

12. The medical instrument according to claim 11, wherein the plurality of rib shaped portions of the path defining part comprises a first pair of rib shaped portions and a second pair of rib shaped portions positioned such that the deviation preventive member is configured to be fitted into a space formed between the first and second pairs of rib shaped portions.

13. The medical instrument according to claim 1, further comprising:

a slider configured to slide relative to the operating part main body between a projection position and a retraction position such that slider restricts the rotation of the bending operating part when the slider is at the projection position and allows the rotation of the bending operating part when the slider is at the retraction position.

14. The medical instrument according to claim 13, wherein the deviation preventive member is configured to be fitted into the path defining part.

15. The medical instrument according to claim 13, wherein the path defining part comprises a plurality of rib shaped portions positioned to surround the plurality of operating lines in the paths.

16. The medical instrument according to claim 15, wherein the plurality of rib shaped portions of the path defining part comprises a first pair of rib shaped portions and a second pair of rib shaped portions positioned such that the deviation preventive member is configured to be fitted into a space formed between the first and second pairs of rib shaped portions.

17. The medical instrument according to claim 1, wherein the bending operating part comprises a dial configured to rotate relative to the operating part main body and to slide between a fixation position and an operation position such that the bending operating part bends the distal portion of the flexible tubular main body by individually applying the pulling force to the plurality of operating lines via rotation of the bending operating part.

18. The medical instrument according to claim 17, further comprising:

a slider configured to slide relative to the operating part main body between a projection position and a retraction position such that slider restricts the rotation of the dial when the slider is at the projection position and allows the rotation of the dial when the slider is at the retraction position.

19. The medical instrument according to claim 18, wherein the path defining part comprises a plurality of rib shaped portions positioned to surround the plurality of operating lines in the paths.

20. The medical instrument according to claim 19, wherein the plurality of rib shaped portions of the path defining part comprises a first pair of rib shaped portions and a second pair of rib shaped portions positioned such that the deviation preventive member is configured to be fitted into a space formed between the first and second pairs of rib shaped portions.

* * * * *